(12) United States Patent
Pandey et al.

(10) Patent No.: US 8,926,646 B2
(45) Date of Patent: Jan. 6, 2015

(54) SURGICAL TOOL

(75) Inventors: Rajesh Pandey, Plantation, FL (US); Charles R. Shambaugh, Jr., Coral Gables, FL (US)

(73) Assignee: HeartWare, Inc., Miami Lakes, FL (US)

( * ) Notice: Subject to any disclaimer, the term of this patent is extended or adjusted under 35 U.S.C. 154(b) by 533 days.

(21) Appl. No.: 12/220,388

(22) Filed: Jul. 23, 2008

(65) Prior Publication Data

US 2009/0030444 A1 Jan. 29, 2009

Related U.S. Application Data

(60) Provisional application No. 60/961,821, filed on Jul. 23, 2007.

(51) Int. Cl.
*A61B 17/00* (2006.01)
*A61B 17/32* (2006.01)

(52) U.S. Cl.
CPC ....... *A61B 17/32* (2013.01); *A61B 2017/00469* (2013.01); *A61B 2017/320056* (2013.01)
USPC ........................................................ 606/190

(58) Field of Classification Search
USPC ................. 606/108, 129, 144, 148, 190, 191; 81/438, 439
See application file for complete search history.

(56) References Cited

U.S. PATENT DOCUMENTS

| | | | |
|---|---|---|---|
| 4,509,516 A * | 4/1985 | Richmond | 606/53 |
| 5,053,043 A * | 10/1991 | Gottesman et al. | 606/148 |
| 5,306,240 A * | 4/1994 | Berry | 604/507 |
| 5,579,668 A | 12/1996 | Kozak | |
| 5,807,338 A * | 9/1998 | Smith et al. | 604/164.01 |
| 5,899,909 A * | 5/1999 | Claren et al. | 606/119 |
| 6,605,094 B1 | 8/2003 | Mann et al. | |
| 7,070,556 B2 * | 7/2006 | Anderson et al. | 600/29 |
| 7,223,229 B2 * | 5/2007 | Inman et al. | 600/30 |
| 2002/0147382 A1 * | 10/2002 | Neisz et al. | 600/29 |
| 2003/0023138 A1 * | 1/2003 | Luscombe | 600/30 |
| 2003/0045892 A1 * | 3/2003 | Kaladelfos | 606/148 |

(Continued)

OTHER PUBLICATIONS

International Search Report issued by the International Searching Authority (ISA/US) in connection with International Application No. PCT/US2008/09016.
Written Opinion of the International Searching Authority issued by the International Searching Authority (ISA/US) in connection with International Application No. PCT/US2008/09016.

(Continued)

*Primary Examiner* — Ryan Severson
*Assistant Examiner* — Rachel S Papeika
(74) *Attorney, Agent, or Firm* — Lerner, David, Littenberg, Krumholz & Mentlik, LLP

(57) ABSTRACT

A tunneling device for creating a pathway in subcutaneous tissue of a person's body. The tunneling device includes a member having two ends, where each of the ends defines an insertion surface that facilitates the insertion of the ends into the subcutaneous tissue of the person's body. The tunneling device includes an interchangeable handle connectable to each of the ends. The handle defines a grasping surface and an opening. The opening is configured to receive either of the ends. The grasping surface enables a user to securely hold the handle with one hand to forcibly move the member through the subcutaneous tissue of the person's body to create the pathway in the subcutaneous tissue, and pull a cable of an implant device through the created pathway.

28 Claims, 13 Drawing Sheets

(56) References Cited

U.S. PATENT DOCUMENTS

| | | |
|---|---|---|
| 2003/0050530 A1* | 3/2003 | Neisz et al. .................. 600/29 |
| 2004/0002724 A1* | 1/2004 | Falahee ....................... 606/185 |
| 2004/0106845 A1* | 6/2004 | Anderson et al. ............. 600/30 |
| 2006/0135949 A1* | 6/2006 | Rome et al. .................. 604/533 |
| 2007/0088343 A1 | 4/2007 | McIntyre et al. |
| 2007/0129719 A1 | 6/2007 | Kendale et al. |

OTHER PUBLICATIONS

International Preliminary Report on Patentability issued by the International Bureau of WIPO in connection with International Application No. PCT/US07/01743.

Written Opinion of the International Searching Authority issued by the International Searching Authority (ISA/US) in connection with International Application No. PCT/US07/01743.

* cited by examiner

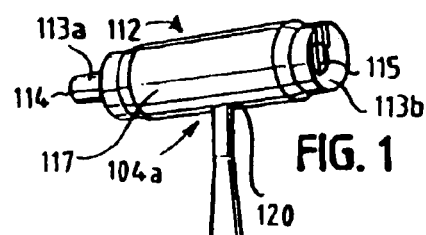
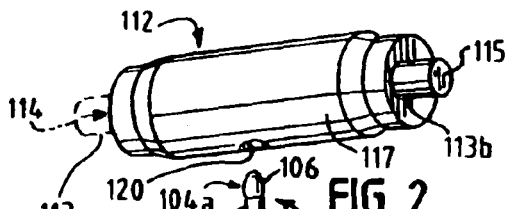
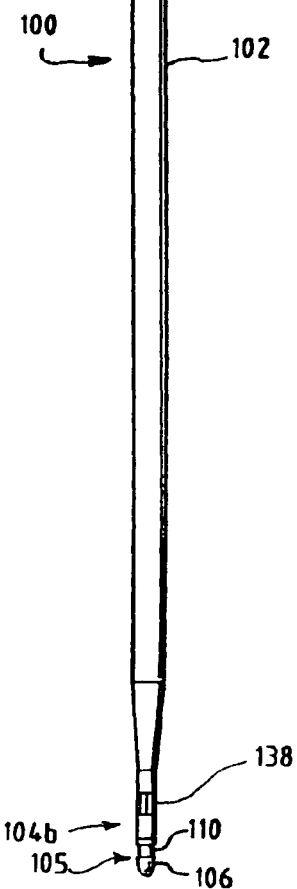
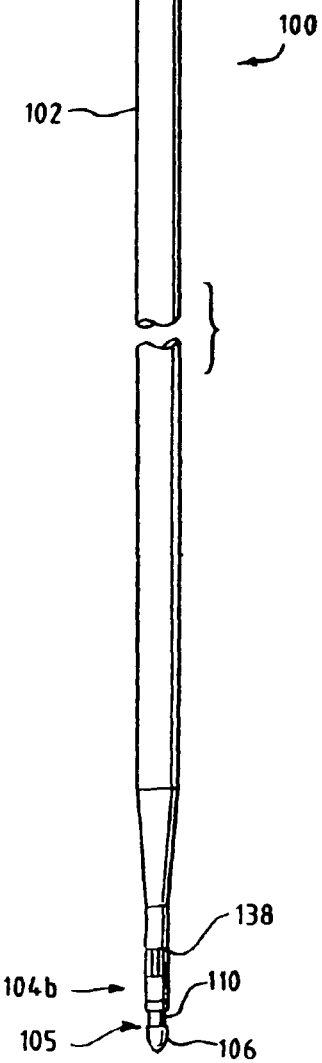

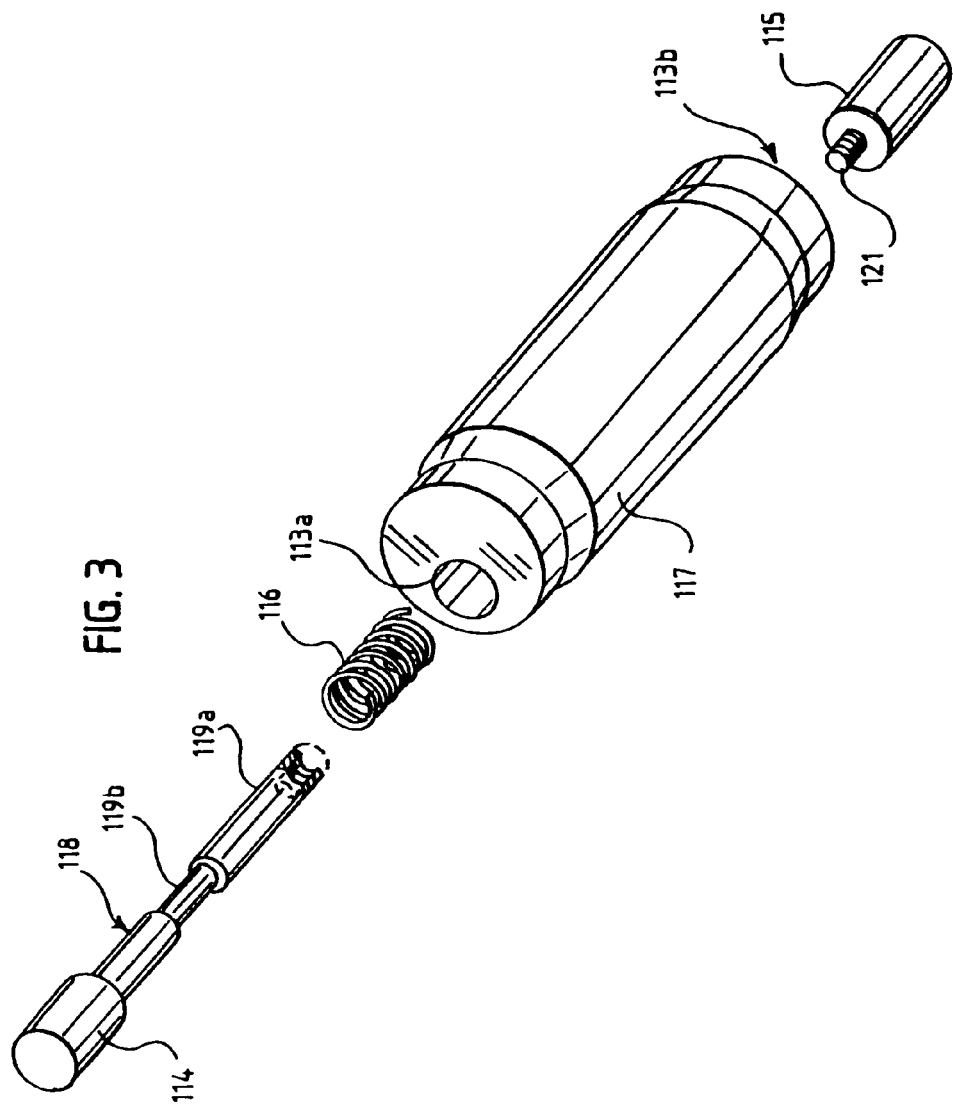

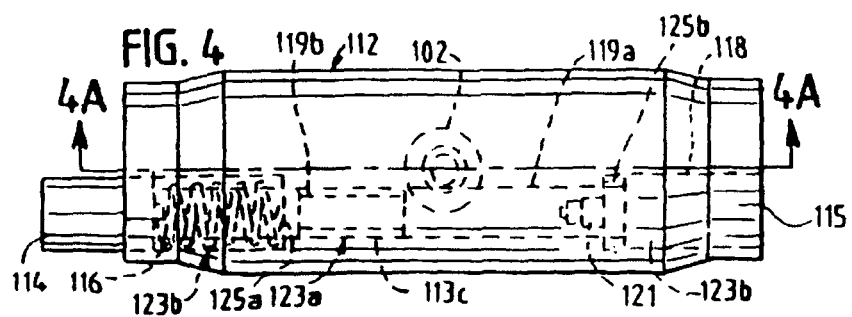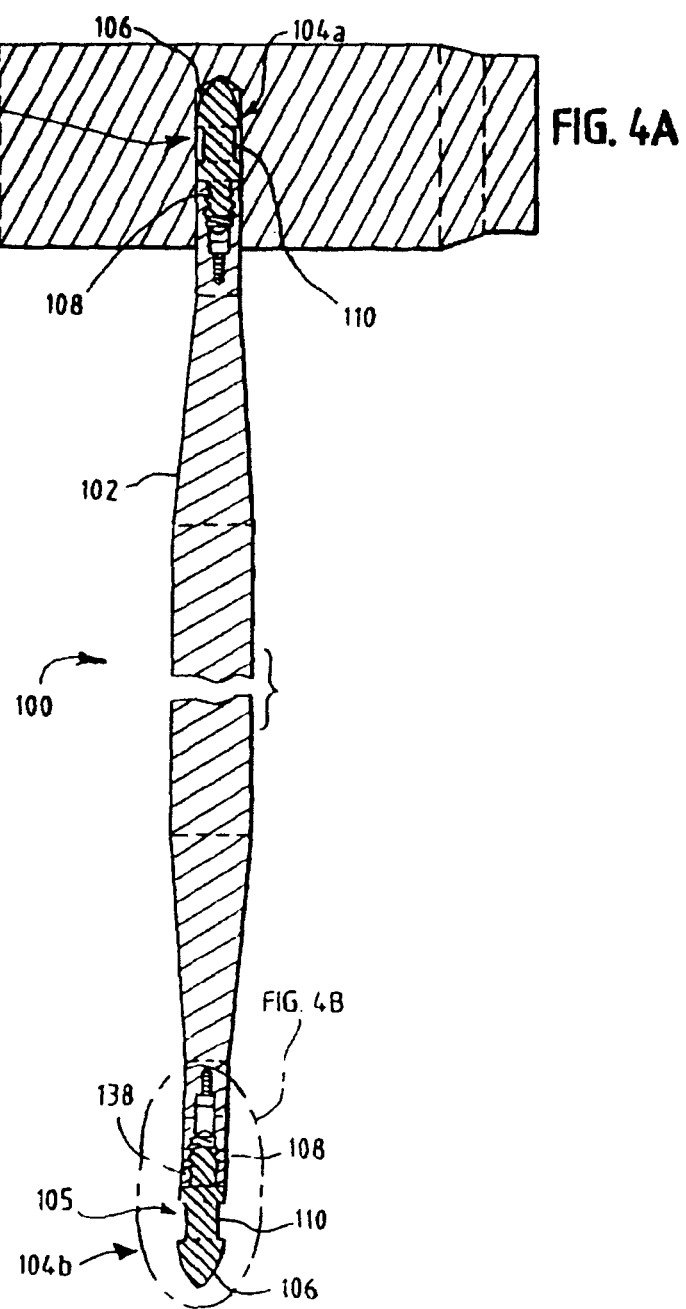

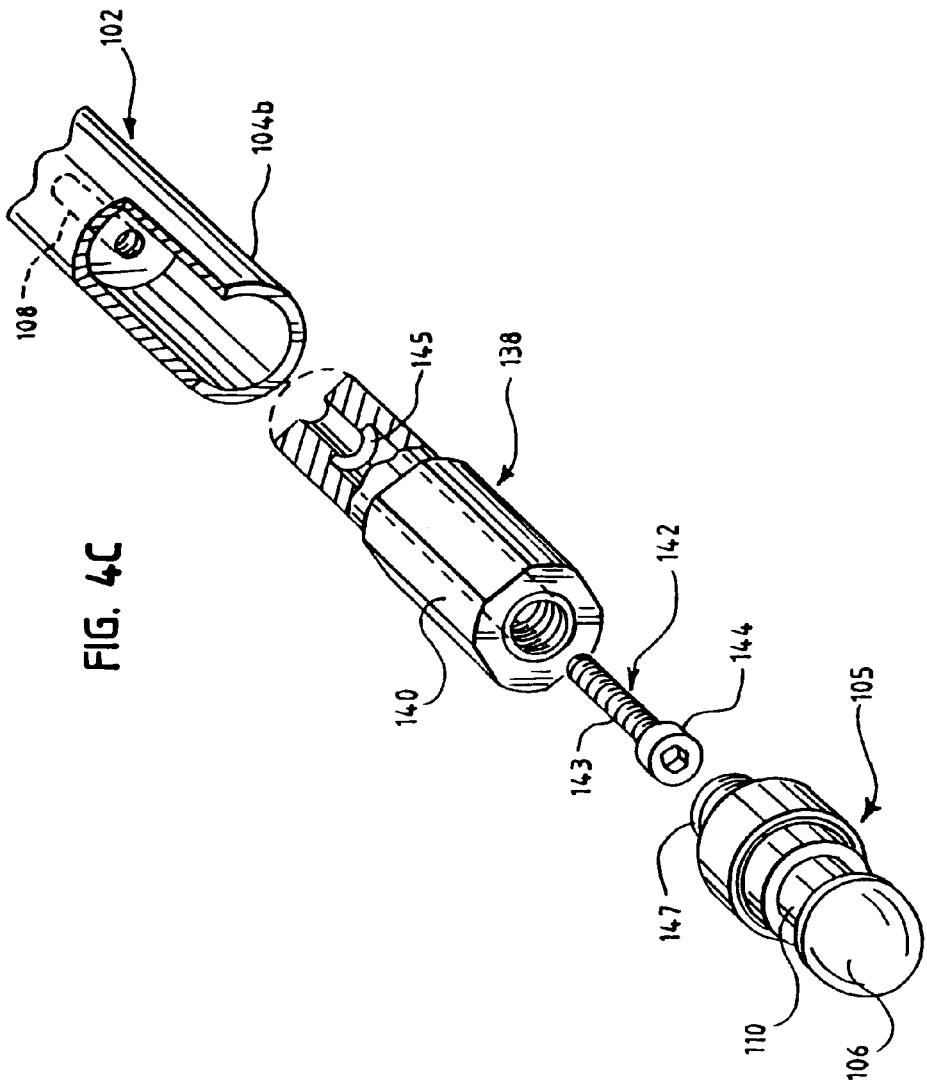

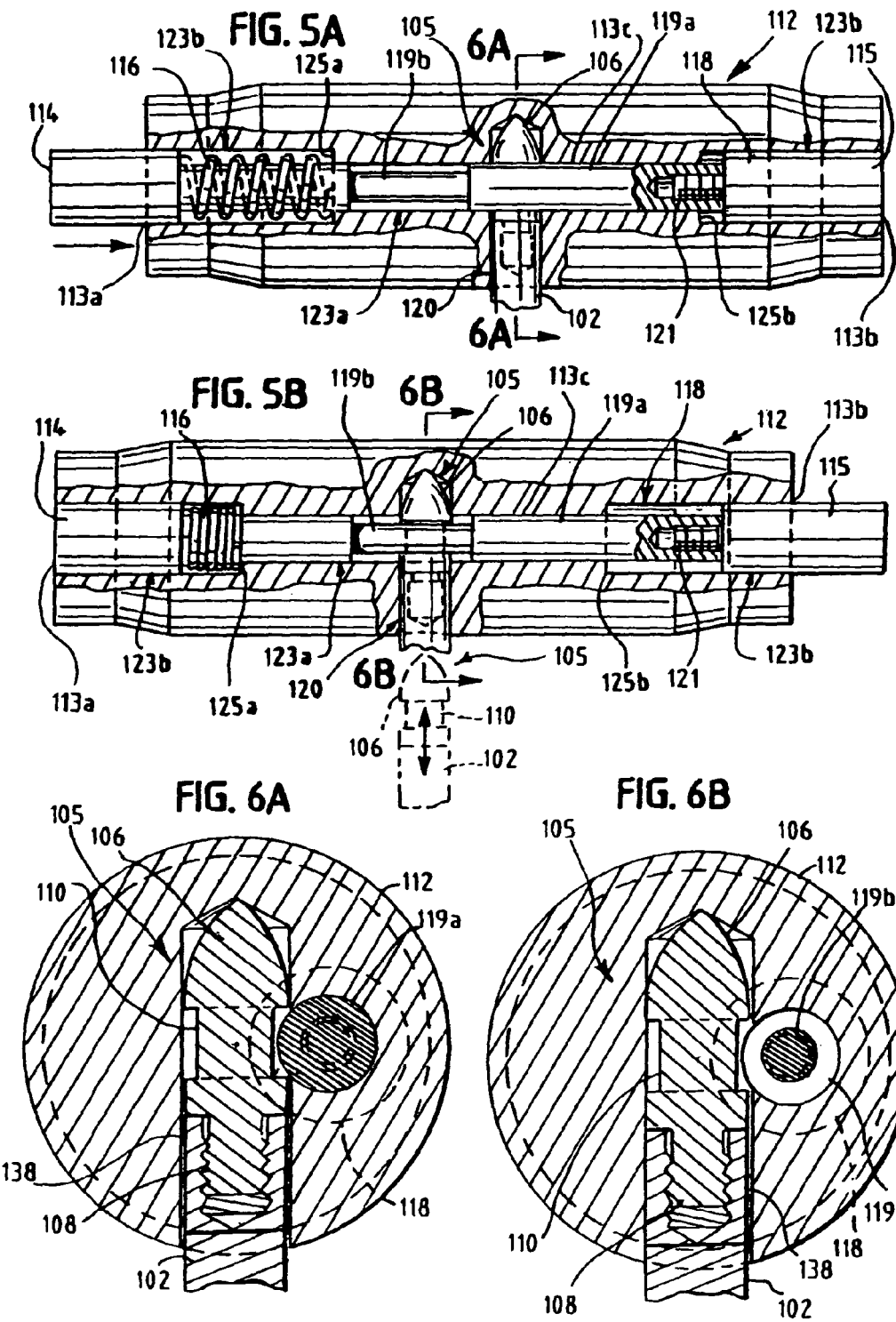

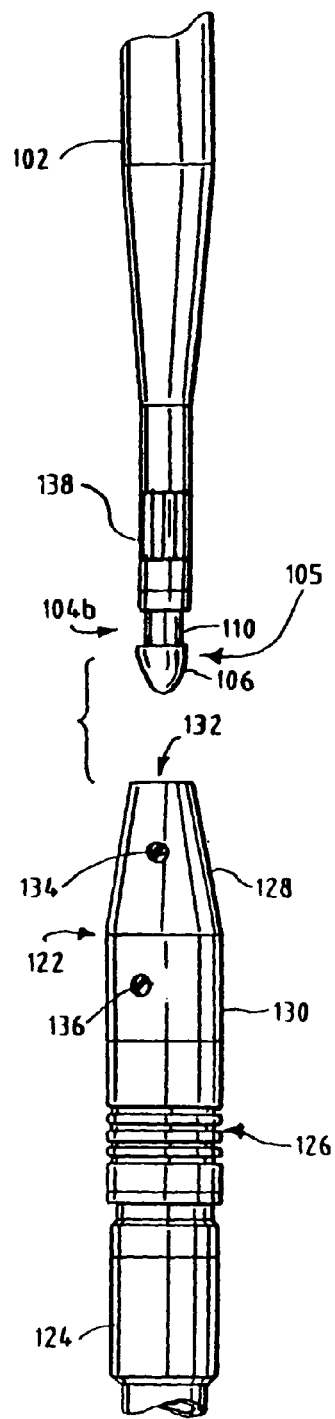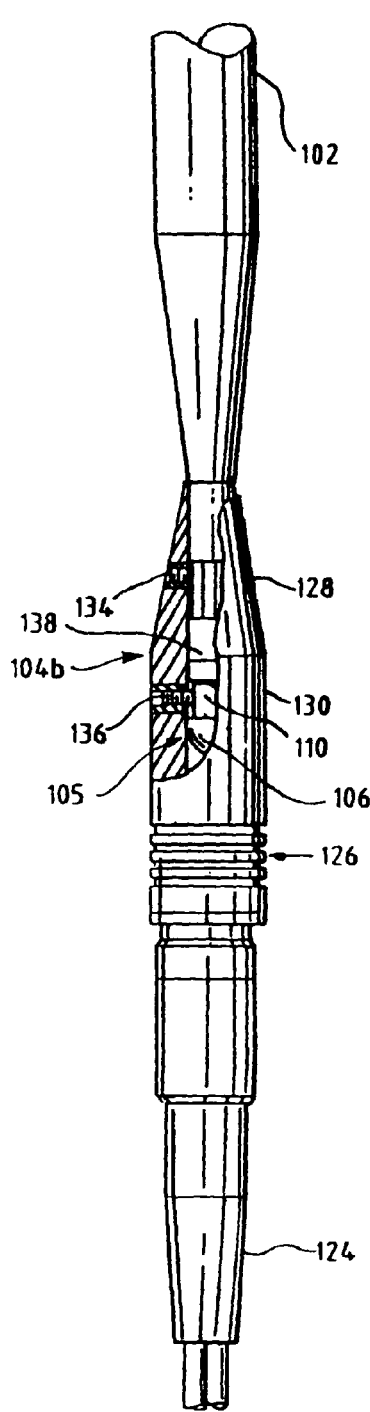

SURGICAL TOOL

This application claims benefit from U.S. Provisional Application No. 60/961,821, filed Jul. 23, 2007, the content of which is hereby incorporated herein by reference into this application.

BACKGROUND OF THE INVENTION

Thousands of heart patients who suffer from severe heart failure could benefit from a heart transplant. However, because of a shortage of donor hearts, most of these patients face a shortened life span characterized by frequent hospitalizations, severe physical disability, and death from congestive failure or cardiogenic shock.

One medical device developed to aid these heart patients is a heart pump such as a left ventricular assist device which enables heart failure patients to return to prolonged and productive lives. A left ventricular assist device ("LVAD") is a battery-operated, mechanical pump-type device that is surgically implanted. It helps maintain the pumping ability of a heart that cannot effectively work on its own.

A LVAD typically includes an electrical cable which is hardwired into the LVAD and routed through a patient's body to an external controller and battery. The surgical procedure of creating a channel or "tunnel" for routing the electrical cable through the body is commonly called "tunneling."

The "tunneling" procedure is an invasive procedure that can lead to infection. Therefore, to minimize the risk of infection and to provide a secure mechanical attachment between the electrical cable and the surrounding tissue, the tunneling channel or path is typically made smaller in size than the electrical connector attached at an end of the electrical cable. The electrical connector is the part of the electrical cable that plugs into or engages the external controller. Usually, the electrical connector is larger in size than the flexible body portion of the electrical cable. As a result, the force required to physically pull the electrical cable through a patient's body is relatively high.

The surgical procedures for creating a tunneling channel or path in a patient's body varies widely. In one procedure, commonly called the outside-in procedure, the tunneling path is created by a tunneling tool, which starts forming the tunnel on the outside of the patient's body. The tunnel goes through the abdominal cavity and up into the thoracic cavity near the LVAD and heart. After the tunnel or pathway is made in the patient's body, the electrical cable is tied to the tunneling tool by a suture or other means. The electrical cable is then dragged or pulled back through the tunneling path using the tunneling tool until a suitable length of the electrical cable extends from the patient's body to connect the electrical cable to the external controller.

In another procedure, commonly called the inside-out procedure, the tunneling path is started from the thoracic cavity inside of the patient's body and continues out through the patient's abdomen and skin to outside of the patient's body. The electrical cable is tied or otherwise connected to the end of the tunneling tool inside the body and pulled through the path to outside the body.

Both of the tunneling procedures described above and other similar procedures employ a relatively high force to pull or drag the electrical cable through the tunnel or path formed in the patient's body. The high stress on the tissues of the body cause trauma to the issues and could lead to complications, infection and extended recovery time for patients.

Additionally, depending on which procedure is used, the design of the tunneling tool may be suitable for one procedure such as the outside-in procedure, but not suitable or usable for another procedure, such as the inside-out procedure.

Accordingly, there is a need for a surgical tool which is adaptable to be used for different tunneling procedures, which is easy to manipulate and use during a tunneling procedure and which minimizes the stress on the body and the risk of infection during the procedure.

SUMMARY OF THE INVENTION

The present invention is directed to a surgical tool and, more specifically, to a surgical tunneling device for creating a pathway in the subcutaneous tissue of the body which is easy to use and adaptable for use in different tunneling procedures.

One embodiment of the present invention provides a tunneling device that includes a malleable member having two ends, where each of the ends defines an insertion surface that facilitates the insertion of the ends into the subcutaneous tissue of the person's body. The tunneling device includes an interchangeable handle connectable to each of the ends. The handle defines a grasping surface and an opening. The opening is configured to receive either of the ends. The grasping surface enables a user to securely hold the handle with one hand to forcibly move the malleable member through the subcutaneous tissue of the person's body to create the pathway in the subcutaneous tissue, and pull a cable of an implant device through the created pathway.

In an embodiment, the tunneling device includes a tip removably connected to at least one of the ends. The tip defines an insertion surface.

In an embodiment, the tunneling device includes a tip removably connected to each of the ends. The tips respectively defining the insertion surface, where at least a portion of each of the ends defines a plurality of threads, and where each of the tips is threadingly engaged with one of the ends of the malleable member.

In an embodiment, the insertion surface defined by at least one of the ends is a tapered surface.

In an embodiment, the insertion surface defined by each of the ends is a tapered surface.

In an embodiment, the tunneling device includes a coupler removably connected to one of the ends of the member. The coupler is adapted to couple the malleable member to an end of the cable.

In an embodiment, the handle includes an actuator, where the actuator is operable to cause the handle to engage with or disengage from one of the ends.

In an embodiment, the handle includes a shaft and a spring positioned between the shaft and the actuator. The actuator is operable to compress the spring and cause the shaft to move to a position where one of the ends of the malleable member is insertable into or releasable from the handle.

Another embodiment provides a tunneling system for creating a pathway in subcutaneous tissue of a person's body. The tunneling system includes a malleable member having a first end and a second end. Each of the ends defines an insertion surface that facilitates the insertion of the first and second ends into the subcutaneous tissue of the person's body. The tunneling device includes an interchangeable handle connectable to each of the first and second ends. The handle defines a grasping surface and an opening. The opening is configured to receive either of the first and second ends and the grasping surface enables a user to securely hold the handle with one hand. The tunneling system also includes a coupler operable to join one of the first and second ends of the malleable member and an end of a cable of an implant device to secure the malleable member and the cable together. The handle is operable to enable a user to forcibly move the malleable member through the subcutaneous tissue of the person's body to create the pathway in the subcutaneous tissue and enable the user to pull the cable of the implant device through the created pathway.

In an embodiment, the handle includes a post and a spring positioned between the post and the actuator. The post has a first diameter and a second smaller diameter. The post is initially positioned adjacent to the first end of the malleable member inserted in the handle to prevent the first end from being removed from the handle. The spring biases the post inwardly to cause the second diameter of the post to be positioned adjacent to the first end of the malleable member to enable the first end of the malleable member to be removed from the handle.

In an embodiment, the insertion surface of at least one of the first and second ends is a tapered surface.

In an embodiment, the insertion surface of each of the first and second ends is a tapered surface.

In an embodiment, the tunneling system includes a removable tip attached to each of the first and second ends, where the removable tips respectively define the insertion surface described above.

In an embodiment, the insertion surface of at least one of the tips is a tapered surface.

In an embodiment, the insertion surface of each of the tips is a tapered surface.

In an embodiment, at least a portion of each of the tips defines a plurality of threads, where each of the tips is threadingly engaged with one of the ends of the member.

In an embodiment, the coupler includes a plurality of connectors. A first connector of the plurality of connectors is operable to secure the coupler to the end of the cable and a second connector of the plurality of connectors is operable to secure one of the first and second ends of the malleable member to the coupler.

Another embodiment provides a method of forming a pathway in subcutaneous tissue of a person's body. The method includes providing a malleable member having two ends, where each of the ends is insertable into the subcutaneous tissue of the person's body. The method includes providing a handle connectable to each of the ends of the member. The handle including an actuator operable to cause the handle to be engaged with and disengaged from one of the ends of the member. The method includes activating the actuator, connecting the handle to one of the ends of the malleable member and inserting the other of the ends into the subcutaneous tissue of the person's body. The method includes moving the other of the ends through the subcutaneous tissue of the person's body to create the pathway in the tissue of the body and connecting a cable of a medical device implanted in the body to the other of the ends. The method includes moving the cable through the pathway created in the body using the handle.

In an embodiment, the method includes connecting a coupler to one of the ends of the malleable member and to an end of the cable.

In an embodiment, the method includes connecting a removable tip to each of the ends. Each of the removable tips defining an insertion surface to facilitate the movement of the tips through the subcutaneous tissue of the body.

It is therefore an advantage of the present invention to provide a surgical tunneling device which enhances the efficiency of a surgical procedure.

Another advantage of the present invention is to provide a surgical tunneling device which is adaptable to be used for different tunneling procedures.

Other objects, features and advantages of the invention will be apparent from the following detailed disclosure, taken in conjunction with the accompanying sheets of drawings, wherein like numerals refer to like parts, elements, components, steps and processes.

DESCRIPTION OF THE FIGURES

FIG. 1 is a perspective view of one embodiment of the surgical tool of the present invention.

FIG. 2 is a fragmentary exploded view of FIG. 1.

FIG. 3 is an exploded view of the handle shown in FIG. 1.

FIG. 4 is a top view of the surgical tool of FIG. 1 where certain parts of the handle and an end of the flexible malleable member are shown in phantom.

FIG. 4A is a cross section view taken substantially along line 4A-4A of FIG. 4.

FIG. 4C is a fragmentary exploded view of an end of the surgical tool shown in FIG. 4A.

FIG. 5A is a partial cut away top view of the surgical tool of FIG. 1 illustrating an end of the flexible malleable member engaged with the handle.

FIG. 5B is a partial cut away top view of the surgical tool of FIG. 1 illustrating the end of the flexible malleable member disengaged from the handle.

FIG. 6A is a cross-section view taken along line 6A-6A in FIG. 5A illustrating the handle engaged with the end of the malleable member.

FIG. 6B is a cross-section view take substantially along line 6B-6B in FIG. 5B illustrating the handle disengaged from the end of the malleable member.

FIG. 7A is a partial side view of the surgical tool of FIG. 1 and an electrical cable illustrating an end of the flexible malleable member of the surgical tool disengaged from an end of the electrical cable.

FIG. 7B is a partial side view of the surgical tool of FIG. 1 and an electrical cable illustrating an end of the flexible malleable member of the surgical tool engaged with the end of the electrical cable.

DETAILED DESCRIPTION

Figure 4B:
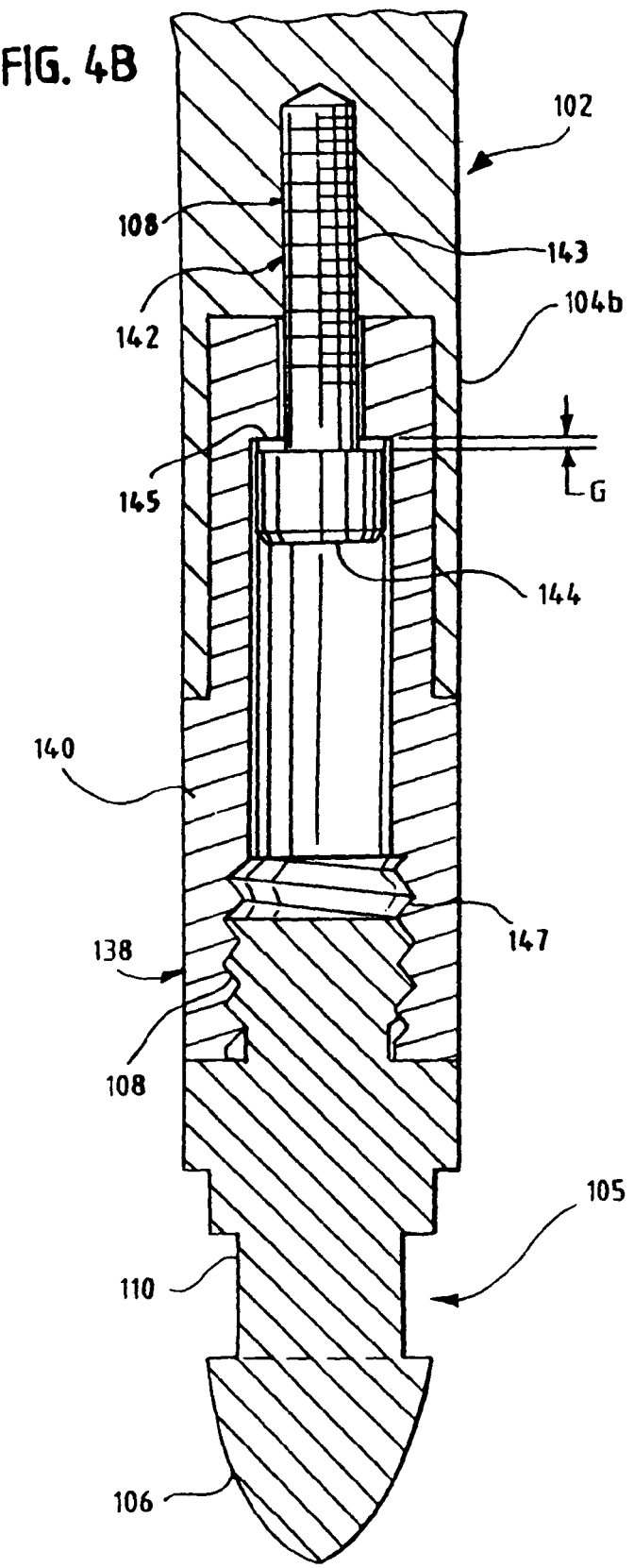
FIG. 4B is an enlarged fragmentary view of an end of the surgical tool shown in FIG. 4A.

The present invention is directed to a surgical tool, and more specifically, to a tunneling device which creates a pathway in the subcutaneous tissue of a person's body for routing cables of an implant device outside of the person's body to allow the communication with and delivery of power to the implant device.

Referring now to the figures, the tunneling device 100 of the present invention includes a flexible or malleable shaft or malleable member 102 which is semi-rigid and bendable to curve or bend through the tissue of a person's body. The malleable member is made of a bendable or flexible material such as 6061 anodized aluminum or any other suitable material or combination of materials. The malleable member 102 may be any suitable size in shape and is generally sized to be slightly smaller than the size or diameter of a cable or wire connected to an implant device, which is routed through a person's body. In one embodiment, shown in FIG. 8, the malleable member 202 is made of alternating sections of varying diameters, including at least a first section 202a having a diameter greater than an adjoining second section 202b. The two sections 202a and 202b may alternate along the length of the malleable member 202. According to this embodiment, the larger diameter sections, such as section 202a, may be used for ease of gripping by the user, whereas the narrower sections, such as section 202b, may be bent. This arrangement of alternating diameters provides sufficient flexibility to the tunneling device to enable the user to bend the tool into different shapes as necessary to facilitate the creation of a pathway through the subcutaneous tissue of the body.

In the illustrated embodiment, the malleable member 102 includes two ends 104a and 104b. In one embodiment, each of the ends 104a and 104b are identical and define an insertion surface which is angled or tapered to facilitate the insertion of the ends into tissue of a person's body.

In one embodiment, a tapered or bullet-like interchangeable removable tip 106 is connected to at least one of the ends 104a and 104b. In another embodiment, the removable tip 105 is connected to each of the ends 104a and 104b. Each tip 105 includes an angled or tapered surface 106 which defines the insertion surface to facilitate the insertion or piercing and movement of the tips through the subcutaneous tissue of the body. In the illustrated embodiment, the tips 105 are made of stainless steel. It should be appreciated that the tips may be made of any suitable material or materials.

Referring to FIGS. 4B and 4C, each end 104a and 104b includes a threaded portion 108 which is threadingly engaged with corresponding threads 142 formed on a portion of the tips 106. Specifically, a cap screw 142 is inserted into an end of the removable tip. The cap screw 142 includes a threaded portion 143 and a head 144. The threaded portion 143 extends through an opening defined by rotating collar 138 and is screwed into the corresponding threaded portions 108 of one or both ends 104a and 104b to hold or secure the collar 138 to the ends 104a and 104b. The cap screw is twisted or screwed into the end of the malleable member 102 so that a gap, G, is formed between the bottom of the head 144 of the cap screw 142 and bottom inside surfaces of the collar 138 as shown in FIG. 4B to allow the collar 138 to freely move or rotate with respect to the end of the malleable member. It should be appreciated that the gap, G, may be any suitable size to allow free rotation of the collar.

The tip 105 defines threads 147 and is screwed into corresponding threads defined by the collar 138 to enable the tips 105 to be secured to the ends 104a and 104b of the malleable member 102. In one example, the tip 105 is screwed into the collar 138 by rotating the tip and holding the collar in place. In another example, the tip 105 is held in place while a user grasps or grips beveled surfaces 140 of the collar 138 and rotates the collar 138 using their fingers or a tool to secure the collar 138 to the cap screw 142. It should be appreciated that the tip 105 may be secured to the collar 138 or the ends 104a and 104b using any suitable connector or connection method.

Referring to FIGS. 3-6B, the handle or grip 112 is connectable to each end 104a and 104b and more specifically, to each tip 106 connected to the ends of the malleable member 102. The handle 112 includes an input, button or actuator 114, a spring 116 positioned adjacent to the actuator and an engagement shaft or post 118 which is positioned adjacent to the spring 116. The handle defines an opening 120 which is positioned on an axis that is transverse to the axis defined by the engagement shaft or post. As shown in FIG. 3, the handle defines end openings 113a and 113b and channel 113c. In one embodiment, the handle 112 is made of 6061 anodized aluminum. It should be appreciated that the handle may be made of any suitable material or materials.

The channel 113c is an elongated opening which extends the length of the handle and includes an axis which is parallel to the axis of the handle. The channel 113c is positioned off-center as shown in FIG. 4. It should be appreciated that the channel 113c may extend along the center of the handle or along any suitable position on the handle. In the illustrated embodiment, the channel 113c includes a central portion or area 123a having a first diameter and end portions or areas 123b each having a second larger diameter than the first diameter. In the illustrated embodiment, the diameters of end portions 123b are the same. In another embodiment, the diameters of the end portions 123b are different. In the illustrated embodiment, the end portions 123b each define a shoulder 125. Specifically, as shown in FIG. 4, one end portion defines shoulder 125a and the opposing end portion defines shoulder 125b.

FIGS. 3 and 4 illustrate the assembly of the handle 112. The button 114 and post 118 are connected together. In one embodiment, the button 114 and post 118 are separate parts which are connected together using any suitable connector or connection method. In another embodiment, the button 114 and post 118 are integrally formed. In the illustrated embodiment, the post 118 is inserted through spring 116 and into the end opening 113a. The post 118 is inserted through channel 113c and is secured in place by cap 115 which is connected to an end of post 118. The cap 115 includes a threaded portion or post 121 which is threadingly engaged with the end of post 118 as shown in FIG. 4. The spring 116 is positioned between the button 114 and shoulder 125a. Shoulder 125a provides a bearing surface for spring 116 so that spring 116 compresses when button 114 is pushed or pressed inwardly and expands when button 114 is released or moves outwardly away from housing 117. Shoulder 125b acts as a stop to prevent cap 115 from moving inwardly past a predetermined distance in housing 117. The position of shoulder 125b determines the distance that button 114 extends from housing 117.

In the illustrated embodiment, the post 118 includes a first diameter 119a and a second diameter 119b. In one embodiment, the first diameter is larger than the second diameter. It should be appreciated that the post may have any suitable number of diameters and the diameters may be the same or different. The handle further defines a grasping or holding surface 117 which is grasped by a user's hand to forcibly push or pull the malleable member 102.

Referring to FIGS. 4, 4A, 4B, 4C, 5A, 5B, 6A and 6B, the opening 120 is adapted to receive one of the ends of the malleable member 102. The end and more specifically, a designated length of the tip 106 connected to the end, is inserted into the opening 120. Once the tip 106 is inserted into the opening 120 of the handle 112, the actuator or button 114 is released and the spring 116 biases the actuator 114 outwardly away from the handle 112. This causes the engagement shaft or post 118 to move in the same direction as the actuator and causes the first diameter 119a of the shaft or post to engage the groove 110 defined by the tip 106 connected to the malleable member 102. The first diameter 119a of the engagement shaft or post 118 engages the groove 110 defined by the tip 106 in such a way that the tip 106 of the malleable member 102 cannot be pulled out of the opening 120 defined by the handle 112. As a result, the end 104a and more specifically, the tip 106 of the malleable member 102 is secured to the handle 112. To release the tip 106 from the handle 112, the button or actuator 114 is activated or pressed to cause the spring 116 to bias the post 118 inwardly within the handle 112. This causes the smaller second diameter section 119b of the post 118 to be positioned over the tip 106 of the malleable member 102. Because the smaller second diameter 119b of the post 118 does not engage the groove 110, the tip 106 of the malleable member 102 is free to move outwardly away from the opening 120 of the handle 112 to be released or removed from the handle. When the end 104a is removed from the handle 112, the button 114 is deactivated or released.

Referring now to FIGS. 7A and 7B, a cap, coupler or coupling device 122 is connected to an end 126 of a cable such as an electrical cable associated with an implant device inserted in a person's body to enable one of the tips 106 of the malleable member 102 to be connected or coupled to the cable 124 to move, pull or push the cable through a tunnel or pathway created by the tunneling device 100 in the body and to minimize or prevent tissues and other contaminants from accumulating on an end of the cable. The coupler 122 includes an angled or tapered portion 128 which defines an opening 132 to receive the end 104b of the malleable member 102. The coupler 122 also includes a straight portion or bottom portion 130 which includes a set screw 134. The set screw 134 is turned or tightened after the coupler 122 is inserted on the end 126 of the cable 124 to secure the coupler to the cable. The end 104b of the malleable member 102 is inserted through the opening 132 defined by the coupler and is secured by a set screw 136 threadingly connected to an inside surface at the tapered portion 128 of the coupler. The set screw 136 is turned and tightened to engage the set screw 136 with the groove 110 formed or defined by the tip 106 of the malleable member 102 to secure the malleable member 102 to the coupler 122. Once secured, the tunneling device 100 can be used to move, push or pull cable 124 through a tunnel path formed in the tissue of the body using the tunneling device 100.

In operation, the tunneling device 100 of the present invention may be used regardless of the surgical procedure employed to create the tunnel or pathway in the tissue of a person's body. For example, the tunneling device 100 may be used to form a tunneled pathway for an inside-out procedure or for an outside-in procedure, as described above. In the outside-in procedure, an end 104a or 104b of the malleable member 102 is inserted into the tissue of a patient's body. The handle 112 is then inserted on the end 104a or 104b of the malleable member 102 that is not inserted into the tissue of the body by pressing or activating the button 114 on the handle 112 and inserting the end of the malleable member 102 into the opening 120 defined by the handle 112. The button 114 is released to secure the handle 112 to the end of the malleable member 102 as described above. The handle 112 is attached to an end 104a or 104b, and more specifically, one of the tips 106 of the malleable member 102 using a single hand which saves time during the surgical procedure.

When the handle 112 is secured to the malleable member 102, a user applies a force to the handle 112 to push the handle 112 inwardly towards the body to cause the inserted end 104a or 104b, and more specifically, the tip 106 of the malleable member 102 to move through the tissue of the body. Once the inserted end of the malleable member 102 reaches the thoracic cavity, the cable 124 of the implant device (not shown) such as a blood pump, is connected to the end of the malleable member 102 using the coupler 122 as described above. When the cable 124 is coupled to the malleable member 102 of the tunneling device 100, the user holds onto the grasping surface 117 of the handle and pulls the handle away from the body to correspondingly pull the inserted end 104a or 104b, or tip 106 of the malleable member 102 and the coupled cable 124 through the tunneled pathway. The cable 124 is pulled through the tunneled pathway by the tunneling device 100 until the cable is pulled a sufficient distance out of the patient's body so that the cable can be connected to a suitable controller, battery or the like.

In an inside-out procedure, one of the tips 106 of the malleable member 102 Is inserted into the tissue near the thoracic cavity by the heart. The handle 112 is secured to the opposite end or tip of the malleable member (i.e., the end or tip not inserted in the tissue), as described above. The handle 112 is then pushed or forced inwardly until the inserted end or tip of the malleable member 102 exits the body through the skin. The handle 112 is then removed by pressing or activating the button 114 to release the handle from the opposite end or tip of the malleable member 102. The handle 112 is then connected on the other end of the malleable member 102 (i.e., the inserted end) by pressing the button 114 and inserting that end or tip of the malleable member 102 into the opening 120 defined by the handle 112. The present invention therefore enables the tunneling device 100 to be used for any surgical tunneling procedure to create a tunnel or pathway in the patient's body. In this procedure, the cable 124 is coupled to the malleable member near the thoracic cavity, and the cable 124 is pulled through the body by pulling on the handle as described above. The tunneling device 100 of the present invention is adaptable to be used in any surgical procedure for creating a tunnel or pathway in the tissue of the body. The tunneling device 100 of the present invention also enables a user to employ a one-handed operation which saves valuable time during a surgical procedure.

Figure 8:
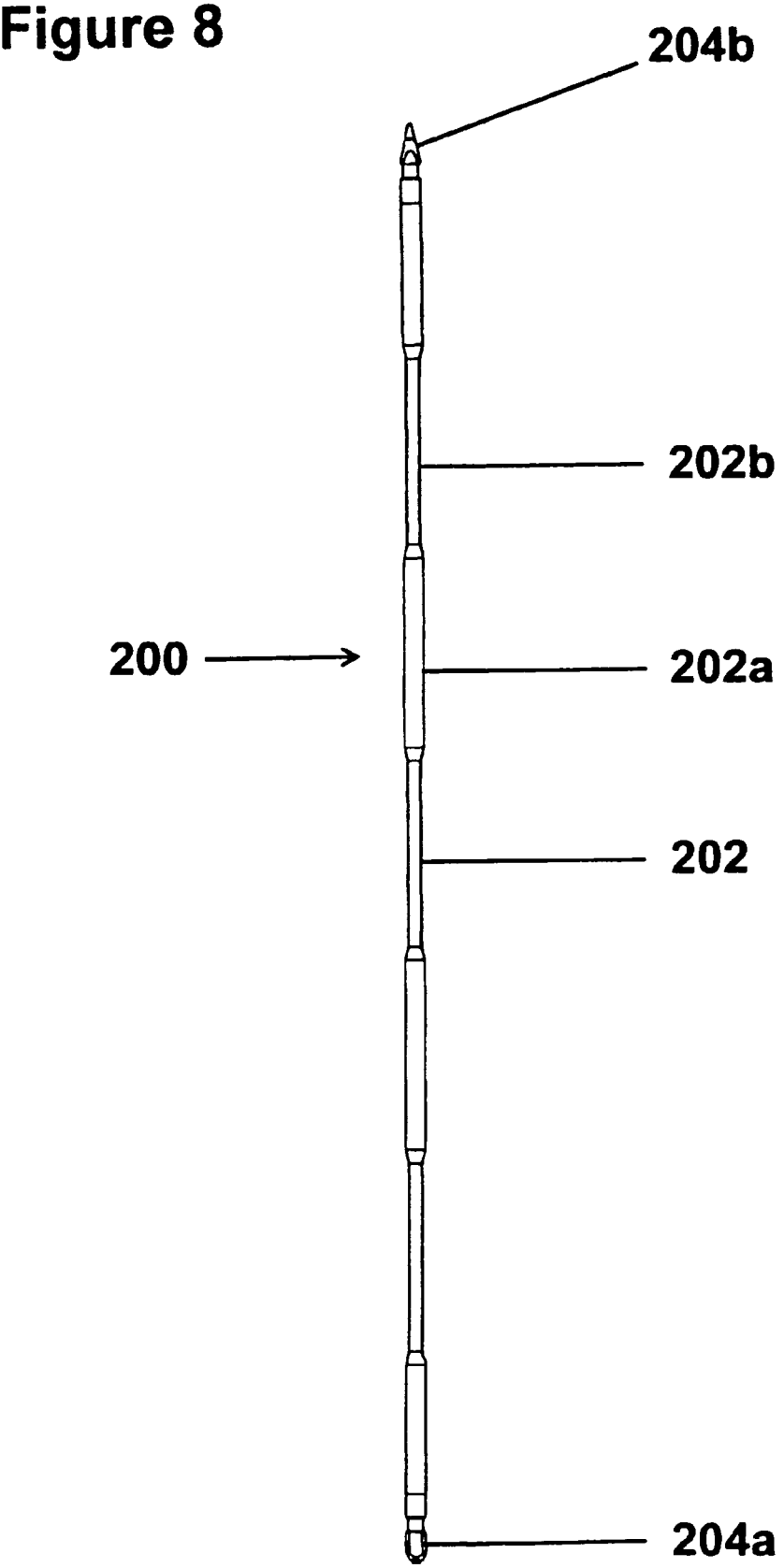
FIG. 8 is a side view of another embodiment of the surgical tool of the present invention.

In another embodiment, as shown in FIG. 8, each of the ends 204a and 204b is different. One end 204b defines an insertion end which has a tapered shape, which may be substantially conical, to facilitate the insertion of the end 204b into and through the subcutaneous tissue of the body. In one embodiment, the tapered outer surface of a conical end may define an angle of substantially 30 degrees. The tip of a conical end may have a radius of 0.020 inches. The other end 204a defines an attachment portion or configuration for engaging and fastening the handle 212, shown in FIG. 11 According to one embodiment, the ends 204a and 204b are formed integrally with the malleable member 202, although other means of defining penetrating and attachment portions of the tunneling tool are within the scope of the present invention.

Figure 9A:
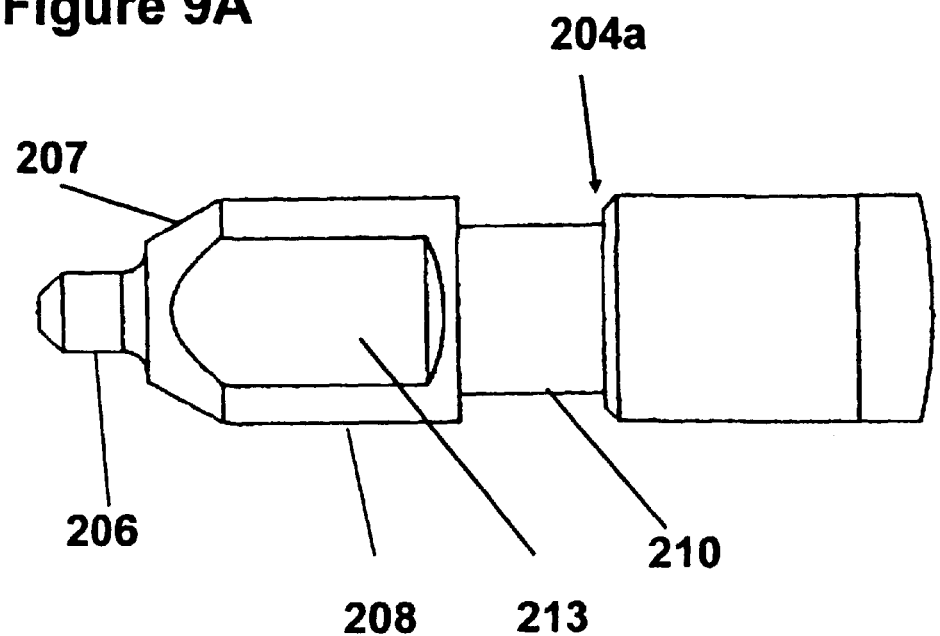
FIG. 9A is an enlarged side view of one end of the surgical tool shown in FIG. 8.
Figure 9B:
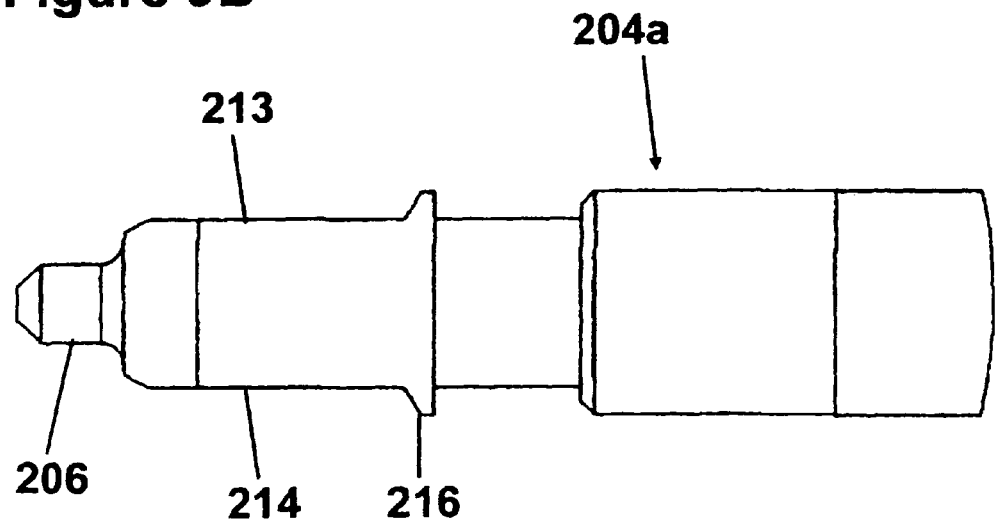
FIG. 9B is an enlarged top view of one end of the surgical tool shown in FIG. 9A.

The attachment end 204a may be generally cylindrical in shape and is shown in FIGS. 9A and 9B. The attachment end 204a includes a narrow tip 206 at a distal end thereof. In one embodiment, the tip 206 has a longitudinal length of about 0.12 inches. Adjacent the tip is an engagement section 208, which may be generally cylindrical, with the exception of two flat peripheral surfaces 213 and 214 which are formed on the outer surface of the attachment end 204a so that the flat surfaces 213 and 214 are disposed in substantially parallel planes on opposite sides of the attachment end 204a. The flat surfaces 213 and 214 do not extend the entire length of the engagement section 208, so that a lip 216 remains at an end opposite the tip 206. A tapered or truncated portion 207 is formed between the tip 206 and the flat surfaces 213 and 214. In one embodiment, the taper portion 207 defines an angle of about 60 degrees to the longitudinal axis of the attachment end 204a. As shown in FIGS. 9A and 9B, a locking section 210 has a reduced diameter compared to the overall diameter of the engagement section 208 and the adjacent diameter of the malleable member 202. The locking section 210 will be used to lock the handle 212 onto the tunneling device 200 and also to lock a coupling device 250 onto the tunneling device 200, as will be described herein.

Figure 11:
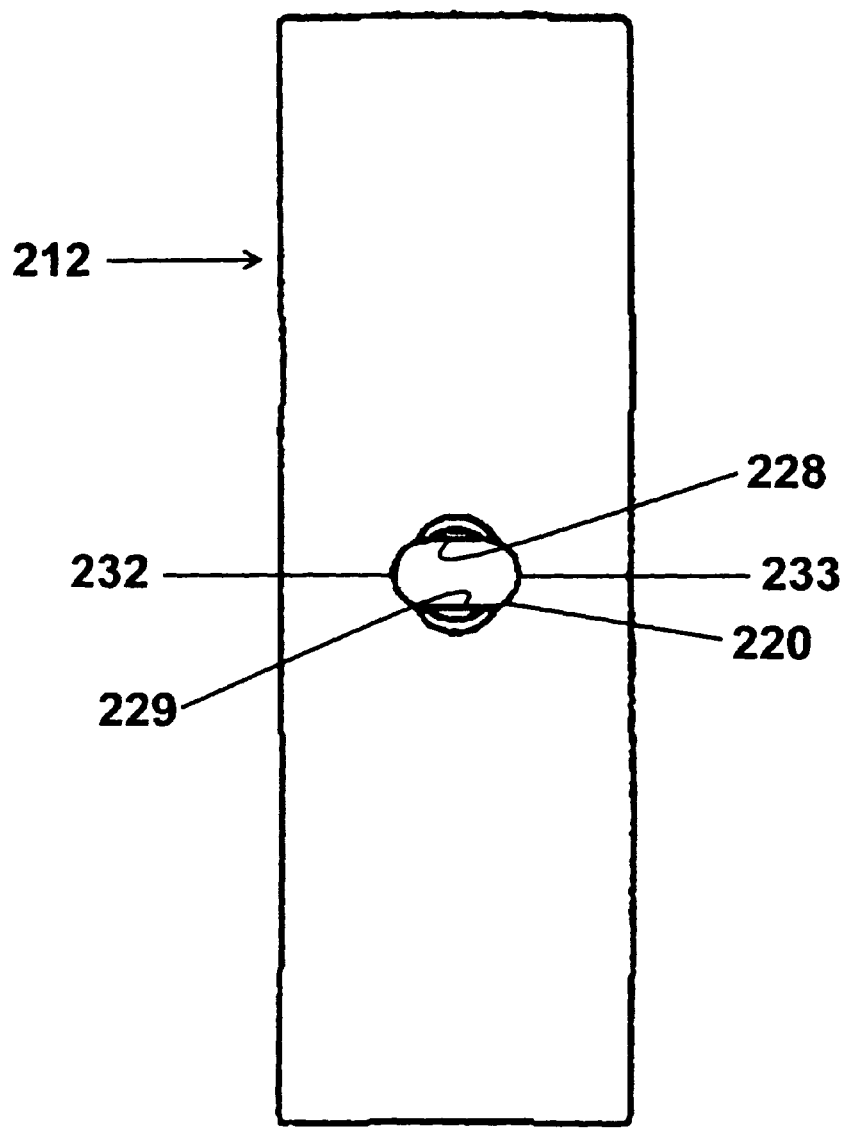
FIG. 11 is a bottom view of the handle according to one embodiment of the present invention.

The flat surfaces 213 and 214 of the engagement section 208 enable the attachment end 204a to engage the handle 212 (FIG. 11), so that the handle 212 may be used to turn the tunneling device 200, as needed. In particular, as shown in FIG. 11, the handle 212 includes a near-elliptical hole 220 formed in a side thereof for receiving the attachment end 204a of the tunneling device 200. The shape of the receiving hole 220 is such that it includes two opposing linear sections 228 and 229 which are connected by semi-circular segments 232 and 233 to form a generally elliptical shape. The linear sections 228 and 229 mate with the flat surfaces 213 and 214 which are formed in the engagement section 208 of the attachment end 204a. According to this construction, the attachment end 204a may be inserted in the receiving hole 220 of the handle 212 such that when the handle 212 is rotated, the malleable member 202 rotates in unison therewith and is unable to rotate independently with respect to the handle 212. The handle 212 engages and locks onto the attachment end 204a of the tunneling device 200 in the same manner as described above in connection with FIGS. 5A and 5B. According to this embodiment, the first diameter 119a of the post 118 engages the locking section 210 of the attachment end 204a in such a way that the attachment end 204a cannot be pulled out of the opening 220 formed in the handle 212, as described herein. The handle 212 is released from the tunneling device 200 in the same manner as described in connection with FIG. 6B, wherein the smaller second diameter 119b of the post 118, engages the locking section 210.

Figure 10A:
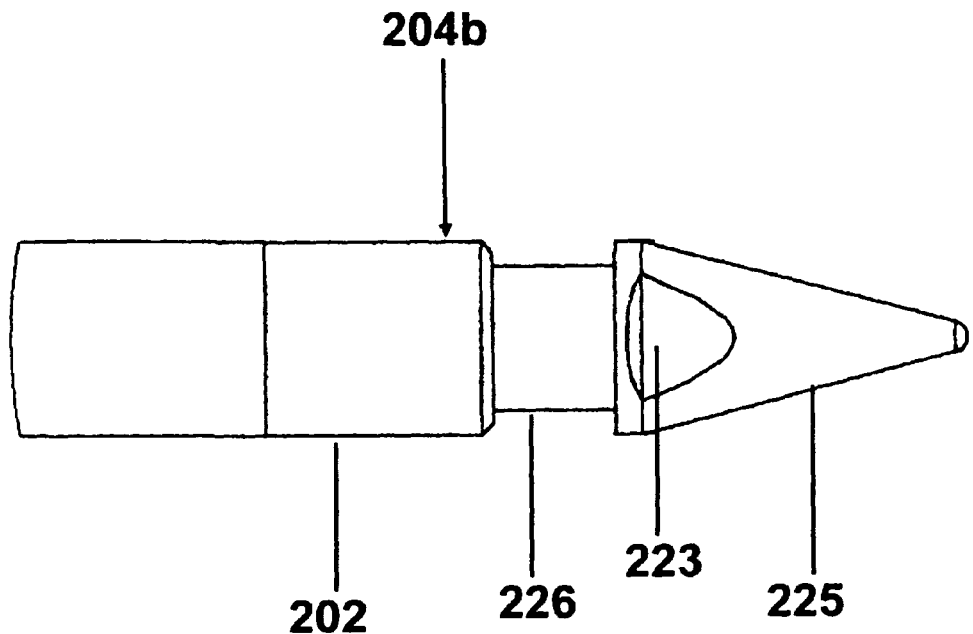
FIG. 10A is an enlarged side view of another end of the surgical tool shown in FIG. 8.
Figure 10B:
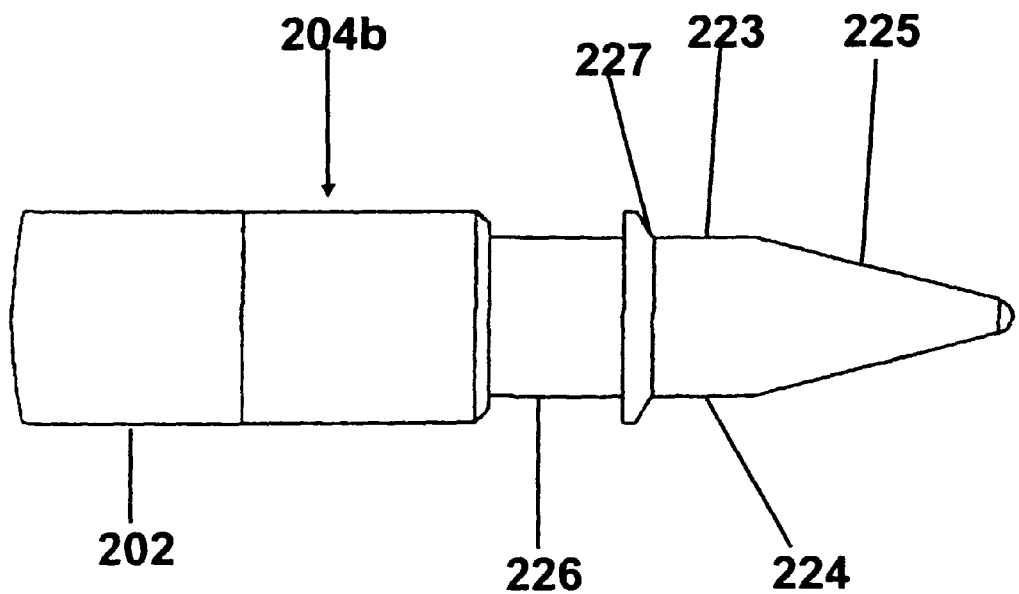
FIG. 10B is an enlarged top view of the end of the surgical tool shown in FIG. 10A.

The insertion end 204b may be generally conical in shape as shown in FIG. 10A. The insertion end 204b includes a conical tip 225 which extends from the end of the insertion end 204b to the reduced diameter, locking section 226. The conical portion of the tip 205 may have a taper of about 30 degrees to the longitudinal axis of the tip 205. The insertion end 204b is conical in shape so as to facilitate insertion of the tunneling member 200 into the subcutaneous tissue of the body. However, the conical tip 225 of the insertion end 204b also has two flat surfaces 223 and 224 which are cut from the conical tip 225 so that the flat surfaces 223 and 224 are disposed in parallel planes on opposite sides of the insertion end 204b, so that the insertion end 204b also may be used with the handle 212. The flat surfaces 223 and 224 do not extend the entire length of the conical tip 225, so that a lip 227 remains at an end opposite the tip 225. As shown in FIGS. 10A and 10B, the locking section 226 has a reduced diameter compared to the adjacent diameter of the malleable member 202. The locking section 226 will be used to lock the handle 212 onto the tunneling device 200 and also to lock the coupling device 250 onto the tunneling device 200, as described herein.

The tunneling device 200, including the attachment end 204a and the insertion end 204b may be made of aluminum or any other suitable material.

Figure 12A:
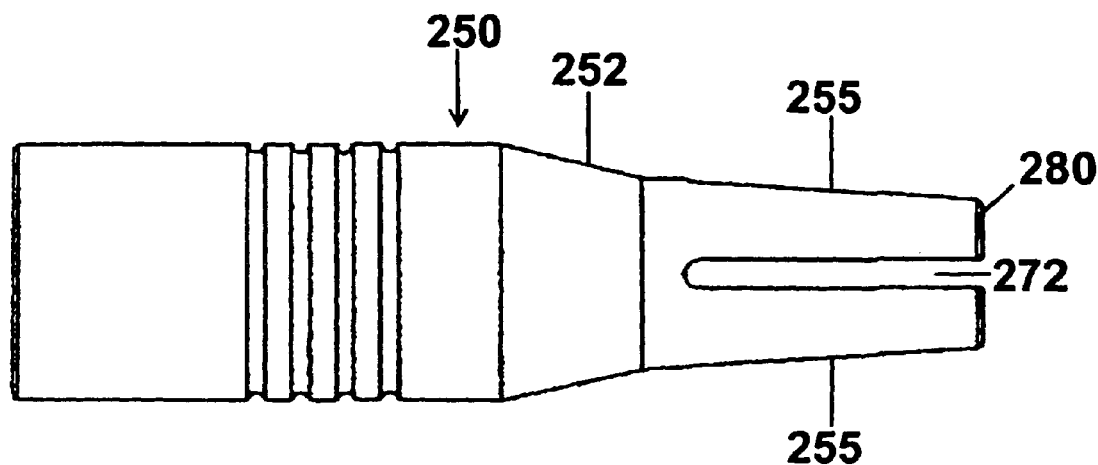
FIG. 12A is an enlarged side view of the cable coupling device according to one embodiment of the present invention.
Figure 12B:
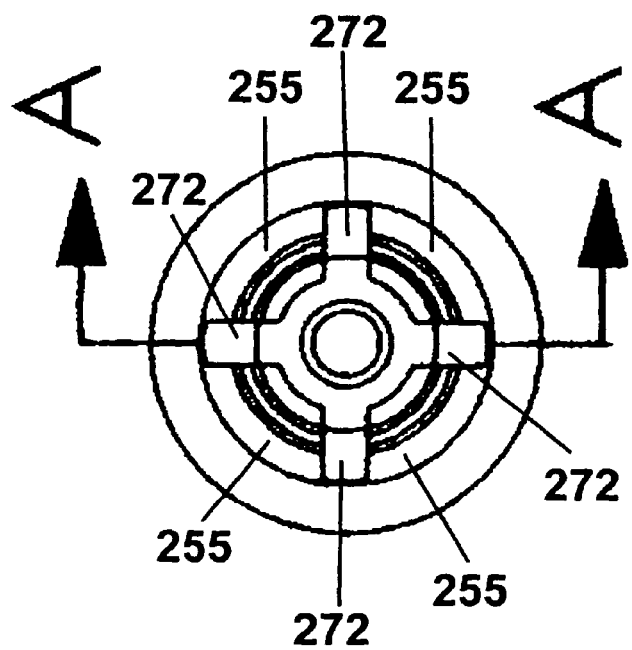
FIG. 12B is a side view of the cable coupling device shown in FIG. 12A.
Figure 12C:
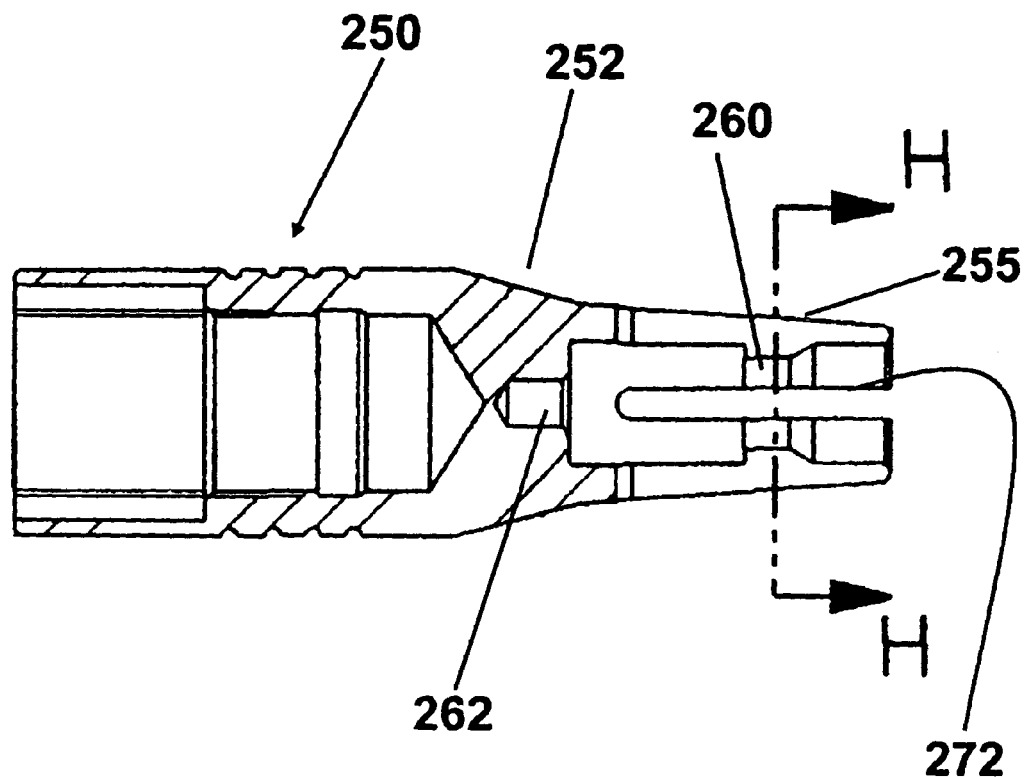
FIG. 12C is an enlarged, cross-sectional view of the cable coupling device taken along line A-A in FIG. 12B.
Figure 12D:
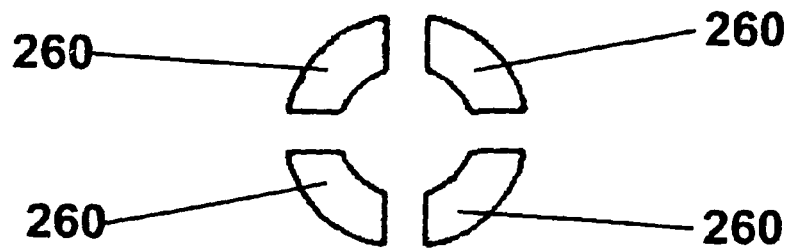
FIG. 12D is a cross-section view taken along line H-H in FIG. 12C.

An alternate embodiment 250 of the coupling device 122 of FIGS. 7A and 7B is illustrated in FIGS. 12A through 12D. The coupling device 250 is similar to the coupling device 122 shown in FIGS. 7A and 7B. The coupling device 250 includes a first tapered portion 252 and a second tapered portion 254 at an end thereof. In one embodiment, the external taper angle 252 is about 15 degrees to the longitudinal axis of the coupling device. The second tapered portion 254 may include a series of four equally-spaced slits 272 extending from a distal end 280 of the coupling device 250 toward the opposite end of the second tapered portion 254. The slits 272 separate the second tapered portion 254 into four prongs 255, each of which has a generally arc shape, as shown in FIG. 12B. The inner surface of each prong 255 includes a projection 260 extending inward. To engage the coupling device 250 with the malleable member 202, one end 204a or 204b of the tunneling device 200 is inserted into the open distal end 280 of the coupling device 250 along the inside surface of each of the prongs 255. As the end 204a or 204b in inserted, the projections 260 abut the engagement section 208 (FIG. 9A) or conical tip 225 (FIG. 10B) and are pressed apart by the tapered sections 207 or 225. When the outer diameter of the inserted end 204a or 204b exceeds the inner diameter of the second tapered portion 254, the prongs 255 cantilever slightly outward until the projections 260 snap into place to engage the locking section 210 or 226, at which point the coupling device 250 is locked in place by a lip 216 or 227. At this point, the tip 206 engages the recess 262 formed in the coupling device 250. Alternatively, the end of the conical tip 225 engages the recess 262. The ability to attach the handle 212 or the coupling device 250 to either end 204a or 204b of the malleable member 202 enables the tunneling device 200 to be used for either outside in or inside out procedures.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims, and this application is limited only by the scope of the claims.

The invention is claimed as follows:

1. A tunneling device for creating a pathway in subcutaneous tissue of a person's body, said tunneling device comprising:
   a member having a first end and a second end, said first end defining a first insertion surface and including at least one flat surface, a locking portion, and a lip positioned between the at least one flat surface and the locking portion and tapering outwardly from the at least one flat surface, and said second end defining a second insertion surface and including at least one flat surface, a locking portion, and a lip positioned between the at least one flat surface and the locking portion and tapering outwardly from the at least one flat surface;
   said member comprising a first cylindrical gripping tunneling section and a second cylindrical gripping tunneling section along a longitudinal axis of said member;
   a cylindrical bendable tunneling section along the longitudinal axis of said member between the first gripping tunneling section and the second gripping tunneling section, said gripping tunneling sections having a greater diameter than said bendable tunneling section;
   a first tapered section between said first gripping tunneling section and said bendable tunneling section;

a second tapered section between said second gripping tunneling section and said bendable tunneling section; and
an interchangeable handle connectable to each of said first end and said second end, said handle defining a grasping surface and an opening, said opening having at least one linear surface mateable with the at least one flat surface of either of the first or second end and said opening configured to receive either of said first end and said second end, said grasping surface enabling a user to securely hold the handle with one hand to forcibly move said member through the subcutaneous tissue of the person's body to create the pathway in the subcutaneous tissue, and sized to facilitate pulling a cable of an implant device through the created pathway.

2. The tunneling device of claim 1, which includes a tip removably connected to at least one of said first end and said second end, said tip defining at least one of said first insertion surface and said second insertion surface.

3. The tunneling device of claim 1, which includes a first tip and a second tip, said first tip removably connected to said first end and said second tip removably connected to said second end, said first and second tips respectively defining said first and second insertion surfaces, wherein at least a portion of each of said first and second ends defines a plurality of threads, and wherein each of said first and second tips is threading engaged with one of said first and second ends of said member.

4. The tunneling device of claim 1, wherein at least one of said first and second insertion surfaces is a tapered surface.

5. The tunneling device of claim 1, wherein each of said first and second insertion surfaces are tapered surfaces.

6. The tunneling device of claim 1, which includes a coupler removably connected to one of said first and second ends of said member, said coupler adapted to couple said member to an end of said cable.

7. The tunneling device of claim 1, wherein the handle includes an actuator, said actuator operable to cause the handle to engage with or disengage from one of said first and second ends.

8. The tunneling device of claim 7, wherein said handle includes a shaft and a spring positioned between said shaft and said actuator, wherein said actuator is operable to compress said spring and cause said shaft to move to a position wherein one of said first and second ends of said member is insertable into or releasable from said handle.

9. A tunneling system for creating a pathway in subcutaneous tissue of a person's body, said tunneling system comprising:
a malleable member having a first end and a second end, each of said ends defining an insertion surface that facilitates the insertion of the first and second ends into the subcutaneous tissue of the person's body and each of the first and second ends including at least one flat surface, a locking portion, and a protruding lip positioned between the at least one flat surface and the locking portion;
said malleable member comprising a first cylindrical gripping tunneling section and a second cylindrical gripping tunneling section along a longitudinal axis of said member;
a cylindrical bendable tunneling section along the longitudinal axis of said malleable member between the first gripping tunneling section and the second gripping tunneling section, said gripping tunneling sections having a greater diameter than said bendable tunneling section;
a first tapered section between said first gripping tunneling section and said bendable tunneling section;
a second tapered section between said second gripping tunneling section and said bendable tunneling section;
an interchangeable handle connectable to each of said first and second ends, said handle defining a grasping surface and an opening, said opening having at least one linear surface mateable with the at least one flat surface of either of the first or second end and said opening configured to receive either of said first and second ends, said grasping surface enabling a user to securely hold the handle with one hand; and
a coupler operable to join one of said first and second ends of said malleable member and an end of a cable of an implant device to secure said malleable member and said cable together,
said handle operable to enable a user to forcibly move said malleable member through the subcutaneous tissue of the person's body to create the pathway in the subcutaneous tissue, and sized to facilitate pulling the cable of the implant device through the created pathway.

10. The system of claim 9, wherein said handle includes a post and a spring, said post having a first diameter and a second smaller diameter,
said post initially positioned adjacent to said first end of said malleable member inserted in said handle to prevent said first end from being removed from said handle, and
said spring biasing said post inwardly to cause said second diameter of said post to be positioned adjacent to said first end of said malleable member to enable said first end of said malleable member to be removed from said handle.

11. The system of claim 9, wherein said insertion surface of at least one of said first and second ends is a tapered surface.

12. The system of claim 9, wherein said insertion surface of each of said first and second ends is a tapered surface.

13. The system of claim 9, which includes a first and second removable tip respectively attached to each of said first and second ends, said first and second removable tips respectively defining said insertion surfaces.

14. The system of claim 13, wherein said insertion surface of at least one of said first and second tips is a tapered surface.

15. The system of claim 13, wherein said insertion surface of each of said first and second tips is a tapered surface.

16. The system of claim 13, wherein at least a portion of each of said first and second tips defines a plurality of threads, and wherein each of said first and second tips are threadingly engaged with one of said first and second ends of said malleable member.

17. The system of claim 9, wherein said coupler includes a plurality of connectors, a first connector of said plurality of connectors operable to secure said coupler to said end of said cable and a second connector of said plurality of connectors operable to secure one of said first and second ends of said malleable member to said coupler.

18. A method of forming a pathway in subcutaneous tissue of a person's body, said method comprising:
(a) providing a member having two ends, each of said ends being insertable into the subcutaneous tissue of the person's body, each of the two ends defining a first insertion surface and including at least one flat surface, a locking portion, and a lip positioned between the at least one flat surface and the locking portion and tapering outwardly from the at least one flat surface;
(b) providing a handle connectable to each of said ends of said member, said handle including an actuator operable to cause the handle to be engaged with and disengaged from one of said ends of said member;

(c) activating said actuator to connect said handle to one of said ends of said member by engaging the handle with the locking portion;

(d) inserting the other of said ends into the subcutaneous tissue of the person's body;

(e) moving said other of said ends through the subcutaneous tissue of the person's body to create the pathway in the tissue of the body;

(f) connecting a cable of an medical device implanted in the body to said other of said ends; and (g) moving said cable through the pathway created in the body using said handle.

19. The method of claim 18, which includes connecting a coupler to one of said ends of said member and to an end of said cable.

20. The method of claim 18, which includes connecting a removable tip to each of said ends, each of said removable tips defining said insertion surface to facilitate the movement of the tips through the subcutaneous tissue of the body.

21. A tunneling device comprising:

a malleable member having two ends, one of said ends defining an insertion element for creating a subcutaneous passage within a person's body, the other of said ends having an engagement surface, and each of said ends including at least one flat surface, a locking portion, and a tapered lip positioned between the at least one flat surface and the locking portion, said member comprising a first gripping tunneling section and a second gripping tunneling section along a longitudinal axis of said member;

a bendable tunneling section along the longitudinal axis of said member between the first gripping tunneling section and the second gripping tunneling section, said gripping tunneling sections having a greater diameter than said bendable tunneling section;

a first tapered section between said first gripping tunneling section and said bendable tunneling section;

a second tapered section between said second gripping tunneling section and said bendable tunneling section;

a handle non-rotatably and releasably connectable to each of said ends, said handle defining a grasping surface and an opening having at least one linear surface mateable with the at least one flat surface of either of the first or second end, said opening configured to receive either of said ends; and a cable coupler non-releasably engageable with said engagement surface, whereby an electrical cable fixed to said cable coupler may be moved through said passage.

22. The tunneling device of claim 21, where said opening of said handle is shaped so that when either of said ends is inserted in said opening, the member turns in unison with the handle.

23. The tunneling device of claim 22, wherein the shape of said opening is oblong.

24. The tunneling device of claim 21, in which said cable coupler is adapted to couple said member to an end of said electrical cable, said coupler comprising projections formed along an inner surface, said projections being adapted to engage a groove formed in said engagement surface thereby to fix said cable coupler to said engagement surface.

25. The tunneling device of claim 21, in which said engagement surface and said insertion element are integral with said malleable member.

26. The tunneling device of claim 25, in which said tunneling device is formed of aluminum.

27. The tunneling device of claim 25, in which said tunneling device is formed of a biocompatible material.

28. A tunneling device for creating a pathway in subcutaneous tissue of a person's body, said tunneling device comprising:

a flexible member having a first end and a second end, said flexible member comprising more than one cylindrical gripping tunneling sections and more than one cylindrical bendable tunneling sections, wherein each gripping tunneling section alternates with each bendable tunneling section along a longitudinal axis of said member, said gripping tunneling sections having a greater diameter than said bendable tunneling sections; and a tapered section between each gripping tunneling section and each bendable tunneling section;

a collar rotatably fastened to said first end of said flexible member allowing rotation of said collar about a longitudinal axis of said first end; and a tip fastened to said collar, said tip including an insertion surface having at least one flat surface, an annular groove between said insertion surface and said collar, and a lip positioned between the flat surface and the annular groove.

* * * * *